(12) United States Patent
Civaroli et al.

(10) Patent No.: US 6,569,452 B1
(45) Date of Patent: May 27, 2003

(54) PHARMACEUTICAL FORMULATIONS IN HYDROXYPROPYLMETHYLCELLULOSE CAPSULES

(75) Inventors: Paola Civaroli, Milan (IT); Lorena Muggetti, Milan (IT); Alessandro Martini, Milan (IT)

(73) Assignee: Pharmacia Italia S.p.A., Milan (IT)

( * ) Notice: Subject to any disclaimer, the term of this patent is extended or adjusted under 35 U.S.C. 154(b) by 0 days.

(21) Appl. No.: 09/857,188

(22) PCT Filed: Jul. 11, 2000

(86) PCT No.: PCT/EP00/06590

§ 371 (c)(1),
(2), (4) Date: Jun. 20, 2001

(87) PCT Pub. No.: WO01/10443

PCT Pub. Date: Feb. 15, 2001

(30) Foreign Application Priority Data

Aug. 10, 1999 (GB) .............................................. 9918885

(51) Int. Cl.[7] .................................................. A61K 9/48
(52) U.S. Cl. ....................... 424/451; 424/452; 424/484; 424/486; 424/462; 514/283; 514/772; 514/778; 514/962

(58) Field of Search ................................. 424/451, 452, 424/484, 486, 462; 514/283, 962, 772, 778

(56) References Cited

U.S. PATENT DOCUMENTS

| | | | | |
|---|---|---|---|---|
| 4,678,516 A | * | 7/1987 | Alderman et al. | 106/197.1 |
| 5,597,829 A | | 1/1997 | Hausheer et al. | 514/283 |
| 5,726,181 A | | 3/1998 | Hausheer et al. | 514/283 |
| 5,756,123 A | * | 5/1998 | Yamamoto et al. | 424/451 |

FOREIGN PATENT DOCUMENTS

| | | |
|---|---|---|
| WO | WO 95/29677 | 11/1995 |
| WO | WO 98/05310 | 2/1998 |
| WO | WO 99/06031 | 2/1999 |

* cited by examiner

Primary Examiner—Thurman K. Page
Assistant Examiner—Lakshmi Channavajjala
(74) Attorney, Agent, or Firm—McDonnell Boehnen Hulbert & Berghoff

(57) ABSTRACT

An oral pharmaceutical formulation, which comprises, in a hydroxypropylmethylcellulose capsule, a camptothecin analogue dispersed or solubilized in a semi-solid matrix of a polyethyleneglycol with a molecular weight ranging from 400 to 20000.

16 Claims, No Drawings

PHARMACEUTICAL FORMULATIONS IN HYDROXYPROPYLMETHYLCELLULOSE CAPSULES

This application is a 371 of PCT/EP00/06590, filed Jul. 11, 2000.

FIELD OF THE INVENTION

The present invention relates to oral dosage forms for camptothecin (CPT) analogues, such as, for example, (S)-[1,4'-Bipiperidine]-1'-carboxylic acid, 4,11-Diethyl-3,4,12,14-tetradydro-4-hydroxy-3,14-dioxo-1H-pyrano[3',4':6,7]indolizino[1,2-b]quinolin-9-yl ester, monohydrochloride, trihydrate also known as irinotecan hydrochloride trihydrate or CPT-11, in hydroxypropylmethylcellulose capsules.

BACKGROUND OF THE INVENTION

CPT-11 is a water-soluble pro-drug of SN-38 (7-ethyl-10-hydroxy-CPT), a biologically potent derivative of the anticancer agent CPT, a topoisomerase I inhibitor. CPT-11 was proven efficacious in a variety of malignancies. Its clinical efficacy has been highlighted by the fact that CPT-11 is the first new active drug to obtain marketing approval in forty years for colorectal cancer.

The intravenous drug form of CPT-11 is currently used for the treatment of colorectal cancer.

It is well known that parenteral administration of antitumor drugs is associated with some intrinsic disadvantages and drawbacks, e.g., patient discomfort or the requirement for the patient to travel to the physician's office for drug administration, with obvious results in patient inconvenience. Thus the need has arisen to find oral formulations of antitumoral drugs that would allow longer dosing regimens, as with continuous infusion, but without the inconvenience or the discomfort of the patient.

Classic oral formulations are, for example, solid oral dosage forms, that are medication delivery systems presented as solid dose units readily administered by mouth. The group includes tablets, capsules, cachets and pills, as well as bulk or unit-dose powders and granules. The group constitutes the most popular form of presentation, and tablets and capsules account for the greatest number of preparations in this category.

It has long been known in the pharmaceutical industries that capsules are a convenient form for the oral administration of a variety of active agents because of their relative ease of manufacture (compared with other dosage forms such as tablets), flexibility of size and dose. Capsules have traditionally been used for powder or granule formulations, but, in recent years, capsules have been adapted to contain the active ingredient in the form of paste, semi-solid or liquid formulation.

Since, for example, CPT-11 is classified as a class I cytotoxic agent, any form of leakage from the dosage form would present a safety concern.

Therefore, formulations as tablets or powder-filled capsules are not as safe and user-friendly as semi-solid filled capsules, since the risks of leakage of the active ingredient from the unit dosage form, both during manufacturing and distribution, is extremely high.

Thus, in light of the above-mentioned problem about the safe handling of CPT-11, it is desirable to formulate CPT-11 as a semi-solid dispersion or solution to be filled into capsules. In particular, a thermoplastic hot-melt type capsule formulation would result in enhanced stability and minimization of leakage concerns.

Furthermore, it is known that the presence of certain active principles and/or of certain ingredients in the filling medium can promote cross-linking in the capsule gelatin shell with the passage of time and/or under stressed conditions. When cross-linking occurs, the gelatin shell becomes less soluble in aqueous media. Cross-linking causes retardation of the disintegration of the capsule shell, and thus retardation of the dissolution of the capsule contents, relative to identical capsules, which have not been subjected to aging or storing at stressed conditions (i.e. temperature and humidity).

Thus, when a filled gelatin capsule contains an ingredient, which promotes cross-linking in the gelatin shell, such as, e.g. a polyethylenglycol (PEG), it is challenging to prepare a formulation, which does not show retarded disintegration and/or dissolution when the formulation grows old.

There is therefore a need to prepare a safe and stable oral encapsulated formulation containing a CPT analogue which does not present neither leakage nor stability problems.

The present invention fulfills such a need by providing stable oral pharmaceutical formulations of CPT analogues which avoid chemical interaction between the active Ingredient and/or the excipients with capsule shells and maintain the dissolution performances of the formulations with aging.

DESCRIPTION OF THE INVENTION

In one aspect of this invention there is provided an oral pharmaceutical formulation, which comprises a camptothecin analogue dispersed or solubilised in a semi-solid matrix, filled into a hydroxypropyl-methylcellulose (HPMC) capsule.

The camptothecin analogue of the present invention is selected from the group comprising: CPT-11, topoteca-n, SN-38, SN-22, 9-amino-20(S)-CPT and 9-nitro-20(S)-CPT.

In particular, the present invention provides an oral pharmaceutical formulation, which comprises CPT-11, dispersed or solubilized into a semi-solid matrix, filled into a hydroxypropylmethylcellulose capsule.

A suitable semi-solid matrix for the formulation according to this invention can be, e.g., a polyethylenglycol (PEG) In the molecular weight range between 400 and 20000, preferably between 1000 and 4000 and specifically 3000, optionally in combination with suitable excipients for semi-solid matrix compositions. Suitable excipients can be, for example, pharmaceutical or food-grade oils, e.g. soya or fractionated coconuts oils; surfactants, e.g. polysorbates; poloxamers, i.e. polyoxyethylene-polyoxypropylene copolymers; solubilising agent, e.g. ethanol and triacetin; natural or synthetic glycerides, e.g. fractionated medium chain glycerides or saturated polyglycol glycerides; or phospholipids.

The formulations according to the invention may be prepared by means of conventional techniques well known to one of ordinary skill in the art.

Typically, the semi-solid matrix to be filled into capsules may be prepared by adding the camptothecin analogue to a molten homogeneous mixture of the excipients. This is then followed by through mixing of the molten mass and capsule filling using standard techniques. Hydroxypropylmethylcellulose capsules are chosen as primary packaging for such a formulation.

For example, the amount of CPT-11 may be in the range of from about 0.2 to about 200 mg, preferably from about 20 to about 100 mg per unit dose.

Generally, a semi-solid matrix formulation is a dispersion or a solution of the active ingredient in thermosoftening hot melt inert carrier prepared by mixing or homogenization.

The obtained semi-solid matrix is therefore filled Into caosuies as liquid using fluid-filling pumps and allowed to solidify at ambient temperature. The major advantage of semi-solid formulations is the safety during manufacturing, being the drug dispersed or dissolved in a liquid mass. At ambient condition such a formulation is solid, providing better chemical stabilitze and minimizing leakage problems.

Selection of suitable excipients for semi-solid matrix formulations is commonly based on physico-chemical, rheological and thermal properties, compatibility with drug and capsule shell as well as on the required drug release profile and bioavailability characteristics of the final dosage form.

In general, thermosoftening materials should have a mewling temperature in the range of about 30° C. to 70° C. and a quite rapid solidification time at ambient condition to avoid any leakage phenomena from capsule after filling and/or during the sealing operation.

Drugs or excipients containing aldehyde groups, or producing aldehyde in decomposition, promote cross-linking in conventional capsules shells made from gelatin, forming a thin insoluble membrane that may delay dissolution.

Moreover, in semi-solid matrix formulations any interaction between the components and the capsule shell is magnified in comparison to powder filled capsules, being the surface contact area between the active ingredients/excipients and the gelatin shell higher.

It can be considered as an unexpected result the fact that the formulations of the present invention are able to guarantee the maintenance of the physico-chemical characteristics of the formulations during manufacturing and storage and to overcome the undesired cross-linking effect, that is practically highlighted by a reduced drug release profile from the dosage forms, especially with aging.

Dissolution rate test results, recovered during accelerated stability studies, as reported in the Examples 1 to 5, clearly demonstrate the increased stability shown by CPT-11 formulations placed into hydroxypropylmethylcellulose capsules according to the invention, when compared with the same CPT-11 formulations placed into conventional hard gelatin capsules.

The following examples are given with the purpose to better illustrate the invention but in no way they must be considered as a limitation of the scope of the invention itself.

It is to be understood that, although the examples reported in the description consider the use of CPT-11 as a representative compound of the camptothecin analogue compounds, the formulation approach according to the invention may be analogously applicable to other camptothecln analogues.

EXAMPLE 1

In the following table 1, the dissolution rate test results, recovered during an accelerated stability study, on Batch ND1216 (CPT-11 semi-solid matrix formulation in PEG100—100 mg CPT-11/capsule—Hard Gelatin Capsule as primary packaging) are shown.

The results are expressed as percent labeled amount (Release %) and its relative standard deviation percent (r.s.d. %) of the active dissolved after 60 minutes in simulated gastric fluid (SGF) without pepsin.

TABLE 1

| Storage (Time/conditions) | Release (%) | r.s.d. (%) | Dissolution medium |
|---|---|---|---|
| Initial | 100.2 | 0.3 | SGF without pepsin |
| 1 month/55° C. | 57.0 | 64.0 | SGF without pepsin |
| 1 month/ 40° C. + 75% R.H. | 74.6 | 20.3 | SGF without pepsin |

R.H. = Relative Humidity

As evident from the above-tabulated data, the release performances of the active from hard gelatin capsules decrease with aging. No chemical degradation of the active, that could justify such a reduction in the dissolution release performances, was observed.

EXAMPLE 2

In the following table 2, the dissolution rate test results, recovered during an accelerated stability study, on Batch D54G01 (CPT-11 semi-solid matrix formulation in PEG100—50 mg CPT-11/capsule—Hard Gelatin Capsule as primary packaging) are shown.

The results are expressed as percent labeled amount (Release %) and its relative standard deviation percent (r.s.d. %) of the active dissolved after 60 minutes in simulated gastric fluid (SGF) without pepsin.

TABLE 2

| Storage (Time/conditions) | Release (%) | r.s.d. (%) | Dissolution medium |
|---|---|---|---|
| Initial | 100.1 | 0.4 | SGF without pepsin |
| 1 month/ 40° C. + 75% R.H. | 56.0 | 67.4 | SGF without pepsin |
| 1 month/ 40° C. + 75% R.H. | 97.5 (1) | 2.2 | SGF without pepsin |

R.H. = Relative Humidity
(1) Dissolution performed on 'capsule content'

As evident from the above-tabulated data, the release performances of the active from hard gelatin capsules decrease with aging. No chemical degradation of the active, that could justify such reduction in the dissolution release performances, was observed.

The good dissolution performance of the formulation stored for 1 month at 40° C. 75% R.H., by removing the content from the gelatin shell before the dissolution testing, is the clear demonstration that the reduction in the release profile is exclusively due to the partial insolubilization of the capsule shell induced by the cross-linking process.

EXAMPLE 3

In the following table 3, the dissolution rate test results, recovered during an accelerated stability study on Batch ND1283 (CPT-11 semi-solid matrix formulation in PEG3000—100 mg CPT-11/capsule—Hard Gelatin Capsule as primary packaging) are shown.

The results are expressed as percent labeled amount (Release %) and as minimum and maximum release percent value of the active dissolved after 60 minutes in simulated gastric fluid (SGF) with and without pepsin.

The use of pepsin is allowed by regulatory authorities in order to overcome the cross-linking issue of hard gelatin capsules. In fact, if the cross-linked gelatin is disrupted by the mechanical forces of gastric emptying or is broken down by digestive enzymes, its formation would not affect absorption and bioavailability of the active. The United States rood and Drug Administration (FDA)/Industry Gelatin Capsule Working Group concluded that formation of an insoluble membrane could be considered to have a negligible impact on drug bioavailability if the capsules dissolved during the 'two-tiered dissolution test' which employs a methods containing digestive enzymes.

TABLE 3

| Storage (Time/conditions) | Release (%) | Minimum and maximum release (%) value | Dissolution medium |
|---|---|---|---|
| Initial | 92.1 | 87.9–97.4 | SGF without pepsin |
| 1 month/55° C. | 9.8 | 5.2–16.8 | SGF without pepsin |
| 1 month/ 40° C. + 75% R.H. | 6.3 | 3.7–11.5 | SGF without pepsin |
| 1 month/55° C. | 89.6 | 91.2–97.4 | SGF with pepsin |
| 1 month/ 40° C. + 75% R.H. | 91.9 | 89.2–96.1 | SGF with pepsin |
| 3 month/ 40° C. + 75% R.H. | 69.6 | 37.6–89.9 | SGF with pepsin |

R.H. = Relative Humidity

It is clearly evident from the above-tabulated data that the addition of pepsin to the dissolution medium is no sufficient to overcome the problem. After 3 month storage at 40° C. and 75%R.H., not even the addition of pepsin to the dissolution medium has allowed obtaining a complete release of the active from the formulation. No chemical degradation of the active, that could justify such reduction in the dissolution release performances, was observed.

EXAMPLE 4

In the following table 4, the dissolution rate test results, recovered during an accelerated stability study, on Batch ND1651 (CPT-11 semi-solid matrix formulation in PEG3000—50 mg CPT-11/capsule—Hydroxypropylmethylcellulose Capsule as primary packaging) are shown.

The results are expressed as percent labeled amount (Release %) and its relative standard deviation percent (r.s.d. %) of the active dissolved after 60 minutes in simulated gastric fluid (SGF) without pepsin.

TABLE 4

| Storage (Time/conditions) | Release (%) | r.s.d. (%) | Dissolution medium |
|---|---|---|---|
| Initial | 101.5 | 2.5 | SGF without pepsin |
| 1 month/55° C. | 100.2 | 10.5 | SGF without pepsin |
| 3 month/ 40° + 75% R.H. | 106.5 | 1.9 | SGF without pepsin |

It is clearly evident from the above-tabulated data that there is not any influence of aging on the release performances of the active from the HPMC formulation. The same unit dosage strength (i.e. 50 mg CPT-11/capsule), packed into hard gelatin capsule, showed reduced dissolution behavior already after 1 month storage at 40° C.+75% R.H. (as above shown in Example 2), while a 3 month storage at the same condition has no effect at all on the dissolution performance of the formulation manufactured into hydroxypropylmethylcellulose capsule. No chemical degradation of the active was observed.

EXAMPLE 5

In the following table 5, the dissolution rate test results, recovered during an accelerated stability study, on Batch ND1655 (CPT-11 semi-solid matrix formulation in PEG3000—100 mg CPT-11/capsule—Hydroxypropylmethylcellulose Capsule as primary packaging) are shown.

The results are expressed as percent labeled amount (Release %) and its relative standard deviation percent (r.s.d. %) of the active dissolved after 60 minutes in simulated gastric fluid (SGF) without pepsin.

TABLE 5

| Storage (Time/conditions) | Release (%) | r.s.d. (%) | Dissolution medium |
|---|---|---|---|
| Initial | 90.3 | 4.1 | SGF without pepsin |
| 1 month/55° C. | 90.2 | 1.6 | SGF without pepsin |
| 1 month/ 40° C. + 75% R.H. | 94.6 | 2.0 | SGF without pepsin |
| 3 month/ 40° + 75% R.H. | 92.3 | 2.0 | SGF without pepsin |

It is clearly evident from the above-tabulated data that there is not any influence of aging on the release performances of the active from the HPMC encapsulated formulation. The same unit dosage strength (i.e. 100 mg CPT-11/capsule), packed into hard gelatin capsule, showed reduced dissolution behavior already after 1 month storage at 40° C.+75% R.H. (as above shown in Example 3), while a 3 month storage at the same condition has no effect at all on the dissolution performance of the formulation manufactured into hydroxypropylmethylcellulose capsule. No chemical degradation of the active was observed.

EXAMPLE 6

In this example, typical semi-solid filling matrices, suitable for hydroxypropylmethylcellulose capsules, are shown. The below mentioned formulae are not intended to be exhaustive or to limit anyway the scope of the invention itself.

|  | mg per capsule | mg per capsule |
|---|---|---|
| FORMULA A | | |
| CPT-11 | 50 mg | 100 mg |
| Polyethylenglycol3000 | 575 mg | 525 mg |
| Fill weight per capsule | 625 mg | 625 mg |
| FORMULA B | | |
| CPT-11 | 50 mg | 100 mg |
| Polyethylenglycol1000 | 575 mg | 525 mg |
| Fill weight per capsule | 625 mg | 625 mg |
| FORMULA C | | |
| CPT-11 | 50 mg | 100 mg |
| Polyethylenglycol3000 | 520 mg | 470 mg |
| Triacetin | 50 mg | 50 mg |
| Polysorbate80 | 5 mg | 5 mg |

-continued

|  | mg per capsule | mg per capsule |
|---|---|---|
| Fill weight per capsule | 625 mg | 625 mg |
| FORMULA D |  |  |
|  |  |  |
| CPT-11 | 50 mg | 100 mg |
| Polyethyleneglycol3000 | 520 mg | 470 mg |
| Polyethyleneglycol400 | 50 mg | 50 mg |
| Polysorbate80 | 5 mg | 5 mg |
| Fill weight per capsule | 625 mg | 625 mg |
| FORMULA E |  |  |
|  |  |  |
| CPT-11 | 50 mg | 100 mg |
| Polyethyleneglycol3000 | 525 mg | 475 mg |
| Gelucire44/14 | 50 mg | 50 mg |
| Fill weight per capsule | 625 mg | 625 mg |

Hydroxypropylmethylcellulose capsules size 0

Another aspect of the present invention provides a method for treating a tumor in a mammal, including a human, which comprises administering to said mammal an oral pharmaceutical formulation of a camptothecin analogue as described in the present invention.

The formulations according to the invention are useful for treating neoplastic diseases, reducing tumor burden, preventing or treating metastasis of neoplasms and preventing recurrences of tumor/neoplastic growths in mammals.

In particular, formulations according to the present invention, wherein the camptothecin analogue is CPT-11, are suitable for the treatment of colorectal cancer.

What is claimed is:

1. An oral pharmaceutical formulation, which comprises:
   in a hydroxypropylmethylcellulose capsule, a camptothecin analogue dispersed or solubilized in a semi-solid matrix of a polyethyleneglycol with a molecular weight ranging from 400 to 20000.

2. A formulation according to claim 1 wherein the camptothecin analogue is CPT-11.

3. A formulation according to claim 2 which comprises from 0.2 to 200 mg per unit dose of CPT-11.

4. A formulation according to claim 3 which comprises from 20 to 100 mg per unit dose of CPT-11.

5. A formulation according to claim 1, wherein the polyethyleneglycol has a molecular weight of from 1000 to 4000.

6. A formulation according to claim 5 wherein the polyethyleneglycol has a molecular weight of 3000.

7. A formulation according to claim 1 which firther comprises an excipient for the semi-solid matrix.

8. A formulation according to claim 7, wherein the excipient is selected from the group consisting of a food-grade glyceride oil, a surfactant, a solubilizing agent, a fractionated medium chain glyceride or a saturated polyglycol glyceride and a phospholipid.

9. A formulation according to claim 2, wherein the amount of CPT-11 is about 0.2 to about 200 mg per unit dose.

10. A formulation according to cliam 9, wherein the amount of CPT-11 is about 20 to about 100 mg per unit dose.

11. A formulation according to claim 1, wherein the camptothecin analogue is selected from the group consisting of 4,11-diethyl-3,4,12,14-tetrahydro-4-hydroxy-3,14-dioxo-1H-pyrano[3',4':6,7]indolizino[1,2-b]quinolin-9-yl ester, monohydrochloride, trihydrate (CPT-11); (S)-10-[(dimethylamino)methyl]-4-ethyl-4,9-dihydroxy-1H-pyrano[3',4:6,7]indolizino[1,2-b]-quinoline-3,14(4H,12H)-dione (topotecan); 7-ethyl-10-hydroxycamptothecin (SN-38); 9-amino-20 (S)-camptothecin and 9-nitro-20(S)-camptothecin.

12. A method of treating neoplastic diseases, comprising:
   administering the oral formulation of claim 1 to a subject suffering from a neoplastic disease.

13. A method according to claim 12, wherein the neoplastic disease is colorectal cancer.

14. A method of reducing tumors, comprising:
   administering the oral formulation of claim 1 to a subject having a tumor thereby reducing the size of the tumor.

15. A method of treating neoplasm metastasis, comprising:
   administering the oral formulation of claim 1 to a subject having suffering from a neoplasm metastasis.

16. A method of preventing recurrences of tumor or neoplastic growths in mammals, comprising:
   administering the oral formulation of claim 1 to a subject having suffering from a recurrence of a tumor or neoplasm growth.

* * * * *

UNITED STATES PATENT AND TRADEMARK OFFICE
CERTIFICATE OF CORRECTION

PATENT NO. : 6,569,452 B1
DATED : May 27, 2003
INVENTOR(S) : Civaroli et al.

It is certified that error appears in the above-identified patent and that said Letters Patent is hereby corrected as shown below:

Column 2,
Line 28, delete "solubilised" and replace with -- solubilized --.
Line 32, delete "topoteca-n" and replace with -- topotecan --.
Line 39, delete "In" and replace with -- in --.

Column 3,
Line 1, delete "Into" and replace with -- into --.
Line 2, delete "caosuies" and replace with -- capsules --.
Line 7, delete "stabilitze" and replace with -- stability --.
Line 16, delete "mewling" and replace with -- melting --.
Line 16, delete both "C." and replace each with -- C. --.
Line 56, delete "camptothecln" and replace with -- camptothecin --.
Line 63, delete "PEG100" and replace with -- PEG1000 --.

Column 4,
Delete Table 1, and replace with the new Table 1 below:

TABLE 1

| Storage (Time/conditions) | Release (%) | r.s.d. (%) | Dissolution medium |
|---|---|---|---|
| Initial | 100.2 | 0.3 | SGF without pepsin |
| 1 month/55° C | 57.0 | 64.0 | SGF without pepsin |
| 1 month/ 40° C + 75% R.H. | 74.6 | 20.3 | SGF without pepsin |

R.H. = Relative Humidity

Delete Table 2, and replace with the new Table 2 below:

TABLE 2

| Storage (Time/conditions) | Release (%) | r.s.d. (%) | Dissolution medium |
|---|---|---|---|
| Initial | 100.1 | 0.4 | SGF without pepsin |
| 1 month 40° C + 75% R.H. | 56.0 | 67.4 | SGF without pepsin |
| 1 month/ 40° C + 75% R.H. | 97.5 (1) | 2.2 | SGF without pepsin |

R.H. = Relative Humidity
(1) Dissolution performed on 'capsule content'

UNITED STATES PATENT AND TRADEMARK OFFICE
CERTIFICATE OF CORRECTION

PATENT NO. : 6,569,452 B1
DATED : May 27, 2003
INVENTOR(S) : Civaroli et al.

It is certified that error appears in the above-identified patent and that said Letters Patent is hereby corrected as shown below:

Column 4, cont'd,
Line 24, delete "PEG100" and replace with -- PEG1000 --.
Line 49, delete "C." and replace with -- C --.

Column 5,
Delete Table 3, and replace with the new Table 3 below:

TABLE 3

| Storage (Time/conditions) | Release (%) | Minimum and maximum release (%) value | Dissolution medium |
|---|---|---|---|
| Initial | 92.1 | 87.9-97.4 | SGF without pepsin |
| 1 month/55° C | 9.8 | 5.2-16.8 | SGF without pepsin |
| 1 month/ 40° C + 75% R.H. | 6.3 | 3.7-11.5 | SGF without pepsin |
| 1 month/55° C | 89.6 | 91.2-97.4 | SGF with pepsin |
| 1 month/ 40° C + 75% R.H. | 91.9 | 89.2-96.1 | SGF with pepsin |
| 3 month/ 40° C + 75% R.H. | 69.6 | 37.6-89.9 | SGF with pepsin |

R.H. = Relative Humidity

Line 31, delete "C." and replace with -- C --.
Delete Table 4, and replace with the new Table 4 below:

TABLE 4

| Storage (Time/conditions) | Release (%) | r.s.d. (%) | Dissolution medium |
|---|---|---|---|
| Initial | 101.5 | 2.5 | SGF without pepsin |
| 1 month/55° C | 100.2 | 10.5 | SGF without pepsin |
| 3 month/ 40° C + 75% R.H. | 106.5 | 1.9 | SGF without pepsin |

Line 66, delete "C." and replace with -- C --.

UNITED STATES PATENT AND TRADEMARK OFFICE
CERTIFICATE OF CORRECTION

PATENT NO. : 6,569,452 B1
DATED : May 27, 2003
INVENTOR(S) : Civaroli et al.

It is certified that error appears in the above-identified patent and that said Letters Patent is hereby corrected as shown below:

Column 6,
Delete Table 5, and replace with the new Table 5 below:

TABLE 5

| Storage (Time/conditions) | Release (%) | r.s.d. (%) | Dissolution medium |
|---|---|---|---|
| Initial | 90.3 | 4.1 | SGF without pepsin |
| 1 month/55° C | 90.2 | 1.6 | SGF without pepsin |
| 1 month/ 40° C + 75% R.H. | 94.6 | 2.0 | SGF without pepsin |
| 3 month/ 40° C + 75% R.H. | 92.3 | 2.0 | SGF without pepsin |

Line 37, delete "C." and replace with -- C --.
Line 51, replace the table with the new table below.

|  | mg per capsule | mg per capsule |
|---|---|---|
| FORMULA A | | |
| CPT-11 | 50 mg | 100 mg |
| Polyethylenglycol 3000 | 575 mg | 525 mg |
| Fill weight per capsule | 625 mg | 625 mg |
| FORMULA B | | |
| CPT-11 | 50 mg | 100 mg |
| Polyethylenglycol 1000 | 575 mg | 525 mg |
| Fill weight per capsule | 625 mg | 625 mg |
| FORMULA C | | |
| CPT-11 | 50 mg | 100 mg |
| Polyethylenglycol 3000 | 520 mg | 470 mg |
| Triacetin | 50 mg | 50 mg |
| Polysorbate80 | 5 mg | 5 mg |

UNITED STATES PATENT AND TRADEMARK OFFICE
CERTIFICATE OF CORRECTION

PATENT NO.   : 6,569,452 B1
DATED        : May 27, 2003
INVENTOR(S)  : Civaroli et al.

It is certified that error appears in the above-identified patent and that said Letters Patent is hereby corrected as shown below:

Column 7,
Line 1, replace the table with the new table below.

|  | mg per capsule | -continued<br>mg per capsule |
|---|---|---|
| Fill weight per capsule | 625 mg | 625 mg |
| FORMULA D | | |
| CPT-11 | 50 mg | 100 mg |
| Polyethylenglycol3000 | 520 mg | 470 mg |
| Polyethylenglycol400 | 50 mg | 50 mg |
| Polysorbate80 | 5 mg | 5 mg |
| Fill weight per capsule | 625 mg | 625 mg |
| FORMULA E | | |
| CPT-11 | 50 mg | 100 mg |
| Polyethylenglycol 3000 | 525 mg | 475 mg |
| Gelucire44/14 | 50 mg | 50 mg |
| Fill weight per capsule | 625 mg | 625 mg |

Hydroxypropylmethylcellulose capsules size 0

Signed and Sealed this

Ninth Day of March, 2004

JON W. DUDAS
*Acting Director of the United States Patent and Trademark Office*